US009045782B2

(12) United States Patent
Marshall et al.

(10) Patent No.: US 9,045,782 B2
(45) Date of Patent: *Jun. 2, 2015

(54) PROCESS FOR THE PRODUCTION OF OPTICALLY-ACTIVE ESTERS OF LACTIC ACID AND LACTYLLACTIC ACID

(75) Inventors: Edward Leslie Marshall, London (GB); Jade Jocelyn Afriye Osei-Tutu, London (GB); Stephen Alexander Calder Smith, London (GB)

(73) Assignee: Plaxica Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/232,365

(22) PCT Filed: Jul. 16, 2012

(86) PCT No.: PCT/GB2012/051698
§ 371 (c)(1),
(2), (4) Date: Jan. 13, 2014

(87) PCT Pub. No.: WO2013/011298
PCT Pub. Date: Jan. 24, 2013

(65) Prior Publication Data
US 2014/0147898 A1 May 29, 2014

(30) Foreign Application Priority Data

Jul. 15, 2011 (GB) .................................. 1112296.7
Jul. 15, 2011 (GB) .................................. 1112297.5
Jun. 11, 2012 (GB) .................................. 1210275.2

(51) Int. Cl.
*C12P 41/00* (2006.01)
*C12P 7/62* (2006.01)
*C12P 7/56* (2006.01)
*C12P 17/06* (2006.01)

(52) U.S. Cl.
CPC ................ *C12P 7/62* (2013.01); *C12P 41/003* (2013.01); *C12P 7/56* (2013.01); *C12P 17/06* (2013.01)

(58) Field of Classification Search
USPC .................................................. 435/139, 135
See application file for complete search history.

(56) References Cited

U.S. PATENT DOCUMENTS

| 2,371,281 | A |   | 3/1945  | Claborn         |         |
|-----------|---|---|---------|-----------------|---------|
| 4,835,293 | A | * | 5/1989  | Bhatia          | 549/274 |
| 5,274,127 | A | * | 12/1993 | Sinclair et al. | 549/274 |
| 6,277,951 | B1|   | 8/2001  | Gruber et al.   |         |
| 7,829,740 | B2|   | 11/2010 | Enomoto et al.  |         |

FOREIGN PATENT DOCUMENTS

| CA | 2734102    | A1 | 3/2010  |
|----|------------|----|---------|
| EP | 0657447    | A1 | 6/1995  |
| GB | 2484674    | A  | 4/2012  |
| JP | 2009195149 | A  | 9/2009  |
| KR | 20050103691| A  | 11/2005 |
| KR | 10-0592794 | B1 | 6/2006  |
| WO | 2004/081220| A2 | 9/2004  |
| WO | 2010/005235| A2 | 1/2010  |
| WO | 2010/105142| A1 | 9/2010  |

OTHER PUBLICATIONS

Emel'yanenko et al, "The Thermodynamic Properties of S-Lactic Acid", Russian Journal of Physical Chemistry A, 2919, 84, No. 9, p. 1491-1497.

Findrik et al, "Evaluation of factors influencing the enantioselective enzymatic esterification of lactic acid in ionic liquid" Bioprocess Biosyst Eng., 2012, 35, p. 625-635.

Groot and Boren, "Life cycle assessment of the manufacture of lactide and PLA biopolymers from sugarcane in Thailand", Int J Life Cycle Assess, 2010, 15, p. 970-984.

Idris and Bukhari, "Immobilized *Candida antarctica* lipase B: Hydration, stripping off and application in ring opening polyester synthesis", Biotechnology Advances, 2012, 30, p. 550-556.

Jeon et al, "Synthesis of alkyl (R)-lactates and alkyl (S,S)-O-lactyl-lactates by alcoholysis of rac-lactide using Novozym 435" Tetrahedron Letters, 2006, 47, p. 6517-6520.

Jeon et al, "Lipase-catalysed enantioselective synthesis of R-lactide from alkyl lactate to produce PDLA (poly D-lactic acid) and stereocomplex PLA (poly lactic acid)", American Chemical Society, 241st ACS National Meeting, Mar. 27-31, 2011, p. 260-261 (Abstract).

Jeon et al, "Improved catalysis of *Candida antarctica* lipase B (CALB) through protein engineering for conversion of R-lactide from alkyl R-lactate in organic solvent", The Korean Society for Biotechnology and Bioengineering, 2011 Spring Meeting, Apr. 14-16, 2011, p. 22.

Kazlaukas et al, "A Rule to Predict Which Enantiomer of a Secondary Alcohol Reacts Faster in Reactions Catalyzed by Cholesterol Esterase, Lipase from *Pseudomonas cepacia*, and Lipase from *Candida rugosa*", J. Org. Chem., 1991. 56, p. 2656-2665.

Lee et al, "Highly Enantioseslective Acylation of rac-Alkyl Lactates Using *Candida antarctica* Lipase B", Organic Process Research and Development, 2004, 8, p. 948-951.

(Continued)

*Primary Examiner* — Ralph Gitomer
(74) *Attorney, Agent, or Firm* — Kramer Levin Naftalis & Frankel LLP

(57) ABSTRACT

A process for treating a mixture of R,R- and S,S-lactide is provided. The process involves contacting the mixture with an aliphatic alcohol and an enzyme to produce a mixture comprising aliphatic ester of lactic acid corresponding to one lactide enantiomer and the aliphatic ester of lactyllactic acid corresponding to the other lactide enantiomer; separating the mixture from the enzyme, and recycling the enzyme to the process; and separating the aliphatic ester of lactic acid from the aliphatic ester of lactyl-lactic acid by fractional distillation. Also provided are processes for the production of S-lactic acid, S,S-lactide, poly-S-lactic acid, R-lactic acid, R,R-lactide, poly-R-lactic acid and stereocomplex polylactic acid.

21 Claims, No Drawings

(56) References Cited

OTHER PUBLICATIONS

Lunt, "Large-scale production, properties and commercial applications of polylactic acid polymers", Polymer Degradation and Stability, 1998, 59, p. 145-152.

Matsumoto et al, "Enzymatic and whole-cell synthesis of lactate-containing polyesters: toward the complete biological polyesters: toward the complete biological production of polylactate", Appl. Microbiol. Biotechnol., 2010, 85, p. 921-932.

Nemeth et al, "Asymmetric Lactic Acid Esterification with Biocatalysts in Ionic Liquid", Hungarian Journal of Industrial Chemistry, 2011, 39, p. 419-425.

Numata et al, "Branched Poly(lactide) Synthesized by Enzymatic Polymerization: Effects of Molecular Branches and Stereochemistry on Enzymatic Degradation and Alkaline Hydrolysis", Biomacromolecules, 2007, 8, p. 3115-3125.

Ohara et al, "Optical resolution of n-butyl D- and L-lactates using immobilized lipase catalyst", Journal of Bioscience and Bioengineering, 2011, 111, p. 19-21.

Shuklov et al, "Studies on the epimerization of diastereomeric lactides", Tetrahedron Letters, 2011, 52, p. 1027-1030.

Smith and Claborn, "Lactic Esters Preparation and Properties", Industrial and Engineering Chemistry, 1940, 32, No. 5, p. 692-694.

Takwa et al, "Rational redesign of *Candida antarctica* lipase B for the ring opening polymerization of D,D-lactide", Chem. Commun., 2011, 47, p. 7392-7394.

Takwa, Lipase Specificity and Selectivity, Doctoral Thesis, Royal Institute of Technology, School of Biotechnology, Department of Biochemistry, Stockholm, Sweden, 2010.

Tsukegi et al, "Racemization behavior of L,L-lactide during heating", Polymer Degradation and Stability, 2007, 92, p. 552-559.

Yang and Liu, "Improved preparation of D, L-lactide from D, L-lactic acid using microwave irradiation", Polymer Bulletin, 2008, 61, p. 177-188.

* cited by examiner

PROCESS FOR THE PRODUCTION OF OPTICALLY-ACTIVE ESTERS OF LACTIC ACID AND LACTYLLACTIC ACID

This application is the United States national phase filing of the corresponding international application number PCT/GB2012/051698, filed on Jul. 16, 2012, which claims priority to and benefit of GB Application No. 1112297.5, filed Jul. 15, 2011; GB Application No. 1112296.7, filed Jul. 15, 2011; and GB Application No. 1210275.2, filed Jun. 11, 2012 which applications are hereby incorporated by reference in their entirety.

The present invention relates to the production of single enantiomers of lactic acid, the cyclic dimer thereof (lactide) or lactate esters. In particular, it relates to a separation process which includes the step of stereoselectively alcoholising a mixture of R,R- and S,S-lactide with an enzyme to produce single enantiomers of different lactic acid derivatives, aliphatic ester of lactic acid and aliphatic ester of lactyllactic acid, which are separated from the enzyme with the enzyme being recycled, and which are separated from each other by fractional distillation.

Lactic acid (2-hydroxypropanoic acid) and its cyclic dimer lactide (3,6-dimethyl-1,4-dioxan-2,5-dione) are becoming increasingly important as building blocks for the chemical and pharmaceutical industries. An example of this is in the use of lactide to manufacture polylactic acid; a polymer whose ability to be produced from a variety of renewable feedstocks and biodegradability makes it an attractive candidate to replace more conventional petrochemical polymers, such as polyethylene terephthalate, for example in the fabrication of food and beverage containers. Today, lactide is made from lactic acid which in turn is typically made by the bacterial fermentation of monosaccharides derived from crops such as maize and other natural products. Lactic acid is chiral and can be made in two enantiomeric forms (respectively L-lactic acid (also referred to as S-lactic acid) on the one hand and D-lactic acid (R-lactic acid) on the other). Derivatives such as lactide are also chiral; lactide in particular exists in two enantiomeric forms (S,S-lactide and R,R-lactide) and a third diastereomeric R,S form sometimes also referred to as meso-lactide. The conventional fermentation technologies referred to above principally generate L-lactic acid with little D-lactic acid being formed. Although these technologies can be modified using different, often genetically engineered, bacteria to produce D-lactic acid in a similarly selective manner, to date the modified bacteria and the associated processes are expensive and difficult to use reliably on a large industrial scale. This is evidenced in the comparatively higher price and limited availability of D-lactic acid.

Polylactic acid is typically prepared in two steps in which lactic acid is first dehydrated to produce lactide and then the lactide is polymerised under carefully controlled conditions to ensure that long polymer chains are produced in preference to shorter oligomers. Since, as explained above, the most readily available source of lactic acid is L-lactic acid, the lactide employed commercially to date has been S,S-lactide and the polymer produced poly-L-lactic acid (PLLA) (also known as poly-S-lactic acid). However the physical properties of PLLA are limited relative to conventional polymers (as are those of the corresponding poly-D-lactic acid (PDLA), also known as poly-R-lactic acid) which to date has limited its utility.

It has been found that these deficiencies can be overcome by using mixtures of PLLA and PDLA which are prepared by, for example, melt blending. It is believed that in these so-called 'stereocomplex' polymer mixtures close packing of the PLLA and PDLA chains occasioned by their differing chirality improves polymer crystallinity which leads to improvements in the properties referred to above. This permits the use of stereocomplex PLA for a much wider range of consumer durable applications, making it a viable alternative to traditional commodity polymers such as polyethylene terephthalate, polypropylene and polystyrene. This approach however requires access to large quantities of PDLA and therefore ultimately to large quantities of D-lactic acid.

In addition to the use of fermentation methods, it is known to produce lactic acid by a conventional chemical transformation. For example, the prior art teaches it can be made by treating monosaccharides derived from a wide range of biological material with aqueous strong base. Such processes however are not stereoselective and generate a racemic mixture of the two enantiomers in approximately equal amounts. They are therefore attractive as a way of making the precursors of stereocomplex polylactic acid. There is a problem however with using racemic lactic acid to make polylactic acid in that the resulting polymer is amorphous and therefore also has poor processing properties. It is therefore necessary to separate the enantiomers present in the racemic lactic acid or those in the corresponding racemic lactide so that the enantiomers of the latter can be polymerised separately and the two chiral polymers mixed only at the final formulation stage.

Separating a racemic mixture into its constituent enantiomers is in general terms a well-known endeavour and strategies adopted have included fractional crystallisation and chromatography. However neither of these methodologies is easy to operate on a large scale, especially in commodity scale polymer manufacturing where throughputs are high and operating costs need to be carefully controlled. What is needed therefore is a simple chemical engineering solution which can be easily and reproducibly operated at scale.

Jeon et al in Tetrahedron Letters 47 (2006) 6517-6520 disclose the laboratory observation that rac-lactide can be alcoholised with various alcohols in the presence of a solvent and the supported lipase enzyme Novozym 435 to produce a product comprising a mixture of the corresponding R-alkyl lactate and the S,S-alkyl lactyllactate. However, this reference goes no further than describing the chemistry.

We have now found a flexible and efficient process that permits the production of aliphatic ester of lactic acid and aliphatic ester of lactyllactic acid on industrial scale in good yield. According to the present invention there is therefore provided a process for treating a mixture of R,R- and S,S-lactide characterised by the steps of:

(a) contacting the mixture of R,R- and S,S-lactide with an aliphatic alcohol and an enzyme to produce a mixture comprising aliphatic ester of lactic acid corresponding to one lactide enantiomer and the aliphatic ester of lactyllactic acid corresponding to the other lactide enantiomer;

(b) separating the mixture comprising aliphatic ester of lactic acid corresponding to one lactide enantiomer and the aliphatic ester of lactyllactic acid corresponding to the other lactide enantiomer from the enzyme, and recycling the enzyme to the process; and (c) separating the aliphatic ester of lactic acid from the aliphatic ester of lactyllactic acid by fractional distillation.

The invention provides a reproducible and scaleable process which provides lactic acid derivatives in high enantiomeric purity and high yield. Preferably, the aliphatic ester of lactic acid obtained from step (c) has an enantiomeric excess of at least 90%, more preferably at least 95%, still more preferably at least 98%, yet more preferably at least 99%. Preferably, the aliphatic ester of lactyllactic acid obtained from step (c) has an enantiomeric excess of at least 90%, more preferably at least 95%, still more preferably at least 98%, still more preferably at least 99%.

Step (a) of the process of the present invention comprises contacting the mixture of R,R- and S,S-lactide with an aliphatic alcohol and an enzyme capable of catalysing the desired transformation. The mixture of R,R- and S,S-lactide may be racemic or scalemic. In one embodiment, the mixture of R,R- and S,S-lactide is racemic. In another embodiment, the mixture of R,R- and S,S-lactide is scalemic (i.e. non racemic).

The lactide used in this stage can in principle be derived from any source but one which is particularly suitable is racemic lactic acid produced by treating a monosaccharide (including glucose, fructose, xylose, and mixtures thereof) or a number of other carbohydrates (including formaldehyde, glyceraldehyde, dihydroxyacetone and glycerol) with a base in aqueous solution at elevated temperature. Especially preferred is the use of a Group IA, Group IIA or quaternary ammonium bases as described for example in GB2484674, the prior art discussed therein, and in U.S. Pat. No. 7,829,740. Typically the racemic lactic acid produced in these processes can be converted into racemic lactide by dehydration processes well-known in the art. It is preferred that the lactide is free or substantially free of the corresponding R,S diastereoisomer (meso lactide). If desired, R,S-lactide may be separated from R,R- and S,S-lactide, for example by routine methods well known in the art.

Suitably the aliphatic alcohol is a $C_1$ to $C_8$ alcohol, preferably a $C_2$ to $C_8$ alcohol, more preferably a $C_3$ to $C_8$ alcohol, most preferably a $C_3$ to $C_4$ alcohol. The aliphatic alcohol is preferably an alkyl alcohol, more preferably a $C_2$ to $C_8$ alkyl alcohol, still more preferably a $C_3$ to $C_8$ alkyl alcohol, yet more preferably a $C_3$-$C_4$ alkyl alcohol. The alcohol may for example be ethanol, n-propanol, i-propanol, n-butanol, s-butanol, i-butanol or 2-ethylhexanol. Examples of preferred alcohols include ethanol, n-propanol, i-propanol, and n-butanol. More preferably the alcohol is i-propanol, n-propanol or n-butanol. Still more preferably the alcohol is n-propanol or n-butanol. In one particularly preferred embodiment the alkyl alcohol is n-butanol. In another embodiment the aliphatic alcohol is i-propanol. In another embodiment the aliphatic alcohol is n-propanol.

Step (a) can be carried out using the aliphatic alcohol as solvent in which case it is preferred that it is chosen so that the mixture of R,R- and S,S-lactide is completely or partially miscible therewith. Thus, in one embodiment step (a) is carried out in the substantial absence of solvent other than aliphatic alcohol (i.e. in that case the alcohol, lactide and/or enzyme may contain some residual solvent, such as water). In other embodiments, other solvent may be present in addition to the aliphatic alcohol (e.g. a co-solvent) in step (a), for example a solvent/co-solvent that is miscible with the aliphatic alcohol. If the mixture of R,R- and S,S-lactide is immiscible or has only low miscibility with the alcohol it is possible and in many cases preferred to employ a solvent/co-solvent with which both components are miscible. Use of a solvent/co-solvent may also lead to further processing advantages in step (c). Typical preferred examples of solvent/co-solvent include unreactive oxygen-containing solvents for example dialkyl ethers (e.g. diethyl ether, dipropyl ether or MTBE), tetrahydrofuran, 1,4-dioxane, glycol ethers, polyalkylene glycol ethers and the like. Ketone solvents/co-solvents are particularly preferred. Preferred ketone solvents include methyl ethyl ketone, methyl isobutyl ketone and, in particular, acetone. Such ketone solvents are particularly suitable for use in processes carried out on an industrial scale, where good solubility properties may be advantageous. Additional hydrocarbon solvents/co-solvents can also be advantageously added. The aliphatic alcohol or the aliphatic alcohol/co-solvent mixture may contain some water. Typically, the aliphatic alcohol or the aliphatic alcohol/co-solvent mixture employed contains less than 1% preferably less than 0.5% by weight water to ensure that the enzyme performs optimally. In some preferred embodiments, molecular sieves are used in the process.

The process may be conducted using excess aliphatic alcohol together with additional solvent/co-solvent. It will be understood that the process may also be carried out using stoichiometric or even sub-stoichiometric quantities of aliphatic alcohol, and the "other" solvent may be the principal or only solvent. Typically the amount of aliphatic alcohol used in step (a) is such that the molar ratio of aliphatic alcohol to lactide is in the range 1:1 to 10:1, preferably 2:1 to 5:1, more preferably 2:1 to 3:1.

The enzyme used in step (a) suitably comprises an esterase which is able to stereoselectively catalyse the reaction of aliphatic ester of lactyllactic acid with aliphatic alcohol to produce aliphatic ester of lactic acid. More preferably, the esterase is a lipase. Preferably the enzyme (e.g. the esterase, lipase) is one which is either chemically or physically immobilised on a porous support for example a polymer resin bead or a silica, alumina or aluminosilicate bead. One particularly preferred example is Lipase B, especially *Candida antarctica* Lipase B, a serine hydrolase with known enantiomeric selectivity towards the hydrolysis of secondary alcohol esters. In this aspect of the invention, the Lipase B is most preferably chemically or physically bound to micro or nano beads made of a polymer resin for example a functionalised styrene/divinylbenzene copolymer or a polyacrylate resin, as is the case for example in the commercially available material Novozym 435 as used in the disclosure by Jeon et al. As Jeon demonstrates, when this particular supported enzyme is used the aliphatic lactate ester enantiomer that is preferentially produced is that derived from R-lactic acid and the remaining aliphatic lactyllactate ester enantiomer is that derived from S-lactic acid. Other preferred enzymes include IMMCALB-T2-150, an immobilised lipase B from *Candida antarctica* covalently attached to dry acrylic beads, manufactured by Chiralvision; IMMCALBY-T2-150, a generic lipase B from *Candida antarctica* covalently attached to dry acrylic beads manufactured by Chiralvision; IMMCALB-T1-350, a lipase B from *Candida antarctica* absorbed on dry polypropylene beads, manufactured by Chiralvision; and cross-linked aggregate of lipase B from *Candida antarctica*, manufactured by CLEA. The enzyme may also be a recombinant *Candida antarctica* lipase B from *Aspergillus oryzae*, supplied by Sigma Aldrich (non-immobilised).

Step (a) is suitably carried out at a temperature in the range of from 15 to 140° C. in order to ensure that reaction rates are significant on the one hand and that the enzyme does not deteriorate with long term use on the other. Preferably the temperature employed is in the range 25 to 80° C. most preferably 30 to 70° C.

Typically, when an enzyme such as a *Candida antarctica* lipase B (e.g. Novozym 435) is used, the aliphatic ester of lactic acid and the aliphatic ester of lactyllactic acid are respectively an aliphatic ester of R-lactic acid and an aliphatic ester of S,S-lactyllactic acid. By varying the reaction conditions it may be possible to alter the enzyme selectivity. Thus in another, less preferred, embodiment the enzyme is a *Candida antarctica* lipase B, and the aliphatic ester of lactic acid and the aliphatic ester of lactyllactic acid are respectively an aliphatic ester of S-lactic acid and an aliphatic ester of R,R-lactyllactic acid.

Step (a) can be carried out on an industrial scale in a number of ways. For example, if a supported enzyme is used the reaction can be carried out batchwise in a single stirred or highly back-mixed tank after which the supported enzyme is separated in step (b), e.g. by filtration or the use of hydrocyclones, and the purified liquid fed to the kettle of the step (c) distillation column. In such a case the residence time of the reactants and the enzyme in the stirred tank will typically be in the range up to 24 preferably up to 10, more preferably from 1 to 8 hours, and the amount of supported enzyme used will be in the range up to 10% preferably up to 5% by weight of the racemic lactide used.

In an alternative preferred embodiment, the process may be operated as a continuous or semi-continuous process. For example, a mixture containing e.g. R,R-lactide and S,S-lactide, alkyl alcohol (e.g. n-butanol) and solvent/co-solvent (e.g. acetone) may be brought into contact with the enzyme (e.g. an immobilised enzyme such as Novozym 435) by passing the mixture through a packed bed of enzyme (e.g. present in a column). In such flow processes, the residency time is selected so as to ensure high conversion. In a particularly preferred embodiment, the packed bed is vertical, and the mixture is fed into the top of the column. Ketone solvents/co-solvents are particularly preferred for use with such processes.

In one preferred embodiment, step (a) is carried out continuously in a tower reactor by for example trickling the liquid reactants down though a fixed or fluidised bed of the supported enzyme contained therein. A product mixture comprising aliphatic ester of lactic acid, aliphatic ester of lactyllactic acid and optionally unreacted lactide, unreacted alcohol and solvent/co-solvent can then be recovered from the bottom of the tower and fed to stage (c). In this arrangement, the contact time of the reactants with the bed is typically in the range of up to 24 hours. Preferably residency times (contact time of the reactants with the bed) are in the range of from 10 minutes to 4 hours, more preferably from 10 minutes to 2 hours. Arrangements of this type permit continuous or semi-continuous generation of product by flow operations.

Where the process is operated in a batch-type reactor, the mixture containing aliphatic ester of lactic acid and aliphatic ester of lactyllactic acid may be separated from the enzyme by, for example, by filtration of the enzyme, or by decanting or siphoning off the mixture prior to distillation. Preferably, in the case of a batch-type process, the enzyme is re-used at least once, more preferably at least twice, still more preferably at least 5 times, yet more preferably at least 10 times, most preferably at least 20 times.

In the case of a process where R,R-lactide, S,S-lactide and alcohol are passed through a packed bed of enzyme (i.e. a continuous or semi-continuous flow process), product and enzyme are continually being separated from one another and the enzyme is continually being recycled. Accordingly, in one preferred embodiment, the process of the invention is a continuous or semi-continuous process which comprises contacting the mixture of R,R- and S,S-lactide with an aliphatic alcohol (e.g. n-butanol) and an enzyme (e.g. Novozym 435), optionally in the presence of a solvent/co-solvent (e.g. acetone) to produce a mixture comprising aliphatic ester of lactic acid corresponding to one lactide enantiomer and the aliphatic ester of lactyllactic acid corresponding to the other lactide enantiomer, by passing a solution containing R,R- and S,S-lactide, aliphatic alcohol and optionally solvent/co-solvent through a packed bed of immobilised enzyme; and separating the aliphatic ester of lactic acid from the aliphatic ester of lactyllactic acid by fractional distillation.

In step (c), the aliphatic ester of lactic acid is separated from the aliphatic ester of lactyllactic acid by fractional distillation, preferably by distillation under reduced pressure.

It has been found that the aliphatic ester of lactic acid and aliphatic ester of lactyllactic acid can be efficiently separated at elevated temperature by fractional distillation without either of the two products undergoing racemisation during this stage. This we believe is surprising given the known tendency of lactic acid derivatives to undergo facile epimerisation. For example Shuklov et al in Tetrahedron Letters 52 (2011) 1027-30 disclose that lactide isomers can undergo reversible epimerisation to generate mixtures of the two enantiomeric lactides and the meso-form even at room temperature. Nishida et al (Polymer Degradation and Stability, 92 (2007) 552-559) have also reported on the racemisation of S,S-lactide at elevated temperatures. In addition, lactic acid derivatives, such as aliphatic esters of lactic acid and/or aliphatic esters of lactyllactic acid, may be susceptible to other undesired side-reactions on heating, for example lactic acid oligomers may be formed.

Once these two components (i.e. aliphatic ester of lactic acid and aliphatic ester of lactyllactic acid) are separated, the fact that they are associated with different enantiomers of lactic acid means that by subsequent chemical transformations they can each be converted to optically pure R,R- and S,S-lactide, or if desired optically pure R- and S-lactic acid which can be used in other non-polymer producing applications.

Preferably, aliphatic ester of lactic acid (e.g. i-propyl lactate, n-propyl lactate, n-butyl lactate) is separated from aliphatic ester of lactyllactic acid (e.g. i-propyl lactyllactate, n-propyl lactyllactate, n-butyl lactyllactate) by fractional distillation at a pressure of from 100 Pa (1 mbar) to 10,000 Pa (100 mbar), more preferably 1,000 Pa (10 mbar) to 5,000 Pa (50 mbar), still more preferably at a pressure of from 2,000 Pa (20 mbar) to 4,000 Pa (40 mbar), yet more preferably at a pressure of from 2,500 Pa (25 mbar) to 3,500 Pa (35 mbar), most preferably at a pressure of about 3,000 Pa (30 mbar). Preferably, aliphatic ester of lactic acid (e.g. i-propyl lactate, n-propyl lactate, n-butyl lactate) is separated from aliphatic ester of lactyllactic acid (e.g. i-propyl lactyllactate, n-propyl lactyllactate, n-butyl lactyllactate) by fractional distillation at a temperature of up to 180° C. (for example at a temperature of from 40° C. to 170° C.), more preferably up to 160, still more preferably up to 140° C., yet more preferably up to 120° C., more preferably at a temperature from 50° C. to 120° C., still more preferably from 50° C. to 110° C., yet more preferably from 52° C. to 110° C., more preferably from 52° C. to 105° C., still more preferably from 75° C. to 105° C., yet more preferably from 90° C. to 105° C., more preferably from 95° C. to 102° C., most preferably at a temperature of about 100° C. In one embodiment, aliphatic ester of lactic acid (e.g. n-butyl lactate) is separated from aliphatic ester of lactyllactic acid (e.g. n-butyl lactyllactate) by fractional distillation at a temperature of from 75° C. to 110° C.

In certain embodiments, aliphatic ester of lactic acid (e.g. n-butyl lactate) is separated from aliphatic ester of lactyllactic acid (e.g. n-butyl lactyllactate) by fractional distillation at a pressure of from 1,000 Pa to 5,000 Pa and at a temperature of up to 180° C., more preferably up to 160° C., still more preferably up to 140° C., yet more preferably up to 120° C. More preferably, aliphatic ester of lactic acid (e.g. n-butyl lactate) is separated by fractional distillation at a pressure of from 1,000 Pa to 5,000 Pa and at a temperature of from 50° C. to 120° C., more preferably from 50° C. to 110° C., yet more preferably from 52° C. to 110° C., more preferably from 52° C. to 105° C., still more preferably from 75° C. to 105° C., yet more preferably from 90° C. to 105° C., more preferably from 95° C. to 102° C., most preferably at a temperature of about 100° C. In one embodiment, aliphatic ester of lactic acid (e.g. n-butyl lactate) is separated from aliphatic ester of lactyllactic acid (e.g. n-butyl lactyllactate) by fractional distillation at a pressure of from 1,000 Pa to 5,000 Pa and at a temperature of from 75° C. to 110° C.

In certain embodiments, aliphatic ester of lactic acid (e.g. n-butyl lactate) is separated from aliphatic ester of lactyllactic acid (e.g. n-butyl lactyllactate) by fractional distillation at a pressure of from 2,000 Pa to 4,000 Pa and at a temperature of up to 180° C., more preferably up to 160° C., still more preferably up to 140° C., yet more preferably up to 120° C. More preferably, aliphatic ester of lactic acid (e.g. n-butyl lactate) is separated by fractional distillation at a pressure of from 2000 Pa to 4000 Pa and at a temperature of from 50° C. to 120° C., more preferably from 50° C. to 110° C., yet more preferably from 52° C. to 110° C., more preferably from 52° C. to 105° C., still more preferably from 75° C. to 105° C., yet more preferably from 90° C. to 105° C., more preferably from 95° C. to 102° C., most preferably at a temperature of about 100° C. In one embodiment, aliphatic ester of lactic acid (e.g. n-butyl lactate) is separated from aliphatic ester of lactyllactic acid (e.g. n-butyl lactyllactate) by fractional distillation at a pressure of from 2,000 Pa to 4,000 Pa and at a temperature of from 75° C. to 110° C.

In certain embodiments, aliphatic ester of lactic acid (e.g. i-propyl lactate, n-propyl lactate, n-butyl lactate) is separated from aliphatic ester of lactyllactic acid (e.g. i-propyl lactyllactate, n-propyl lactyllactate, n-butyl lactyllactate) by fractional distillation at a pressure of from 2,500 Pa to 3,500 Pa and at a temperature of up to 180° C., more preferably up to 160° C., still more preferably up to 140° C., yet more preferably up to 120° C. More preferably, aliphatic ester of lactic acid (e.g. n-butyl lactate) is separated by fractional distillation at a pressure of from 2,500 Pa to 3,500 Pa and at a temperature of from 50° C. to 120° C., more preferably from 50° C. to 110° C., yet more preferably from 52° C. to 110° C., more preferably from 52° C. to 105° C., still more preferably from 75° C. to 105° C., yet more preferably from 90° C. to 105° C., more preferably from 95° C. to 102° C., most preferably at a temperature of about 100° C. In one embodiment, aliphatic ester of lactic acid (e.g. n-butyl lactate) is separated from aliphatic ester of lactyllactic acid (e.g. n-butyl lactyllactate) by fractional distillation at a pressure of from 2,500 Pa to 3,500 Pa and at a temperature of from 75° C. to 110° C.

In certain embodiments, aliphatic ester of lactic acid (e.g. n-butyl lactate) is separated from aliphatic ester of lactyllactic acid (e.g. n-butyl lactyllactate) by fractional distillation at a pressure of about 3,000 Pa and at a temperature of up to 180° C., more preferably up to 160° C., still more preferably up to 140° C., yet more preferably up to 120° C. More preferably, aliphatic ester of lactic acid (e.g. n-butyl lactate) is separated by fractional distillation at a pressure of about 3,000 Pa and at a temperature of from 50° C. to 120° C., more preferably from 50° C. to 110° C., yet more preferably from 52° C. to 110° C., more preferably from 52° C. to 105° C., still more preferably from 75° C. to 105° C., yet more preferably from 90° C. to 105° C., more preferably from 95° C. to 102° C., most preferably at a temperature of about 100° C. In one embodiment, aliphatic ester of lactic acid (e.g. n-butyl lactate) is separated from aliphatic ester of lactyllactic acid (e.g. n-butyl lactyllactate) by fractional distillation at a pressure of about 3,000 Pa and at a temperature of from 75° C. to 110° C.

The distillation column used may optionally contain packing in order to achieve improved separation efficiencies, for example Raschig rings or structured packing.

In step (c), at least the lower boiling aliphatic lactate ester fraction is removed overhead for further use or treatment thereby indirectly effecting separation of the two lactic acid enantiomers. In a preferred embodiment, the aliphatic ester of lactic acid is removed overhead by distillation, and the distillation residue comprises the aliphatic ester of lactyllactic acid, which may be removed via a side stream. In an alternative embodiment, both the aliphatic ester of lactic acid and the aliphatic ester of lactyllactic acid are removed overhead by distillation (e.g. they are collected as separate overhead product streams, for example at different temperatures and/or pressures).

The distillation column (also known as a fractionation column) used for step (c) must have the necessary number of theoretical plates to perform its function (i.e. to enable separation of aliphatic ester of lactic acid from aliphatic ester of lactyllactic acid). In the case where the reaction is carried out batchwise the reaction will likely have gone to completion and the residuum in the boiler of the distillation column will generally comprise an aliphatic lactyllactate ester fraction which can then be removed by a side stream for its own further treatment and use. If steps (a) and (b) are operated continuously then the distillation column in step (c) may also operate continuously with recycle to ensure that at steady state all of the R,R- or S,S-lactide is converted quantitatively (as the case may be) to aliphatic ester of S-lactic acid or aliphatic ester of R-lactic acid, and that the corresponding aliphatic ester of lactyllactic acid is recovered in single enantiomeric form. In this continuously operated case the distillation can be effected in either a single column or a train of columns arranged in series. Typically the distillation column(s) used in step (c) are operated at a pressure of less than 5,000 Pa.

In an embodiment of the present invention the single enantiomer of the aliphatic lactate ester recovered in step (c) can be converted to either the corresponding lactic acid enantiomer or to the corresponding lactide enantiomer. In both cases, the aliphatic alcohol is released and can be separated and recycled to step (a). For example, in the case where the supported enzyme used is Novozym 435, the alcohol is n-butanol and the solvent is acetone, the R-n-butyl lactate so generated can be converted to R-lactic acid or R,R-lactide. If R,R-lactide is produced it can then be polymerised to produce optically pure PDLA. Likewise, the single enantiomer of the aliphatic lactyllactate ester if recovered in pure form in step (c) can be converted back to either the corresponding lactic acid or lactide enantiomer so that for example in the case that the aliphatic ester of lactyllactic acid is S,S-n-butyl lactyllactate, it can be hydrolysed to S-lactic acid or converted into S,S-lactide, which can then be polymerised to produce optically pure PLLA.

Thus, according to a first further embodiment of the present invention there is provided a process for producing S-lactic acid characterised by the steps of: contacting a mixture of R,R- and S,S-lactide with an aliphatic alcohol (e.g. a $C_1$ to $C_8$ alkyl alcohol) and an enzyme to produce a mixture comprising aliphatic ester of lactic acid corresponding to one lactide enantiomer, and aliphatic ester of lactyllactic acid corresponding to the other lactide enantiomer; separating the mixture comprising aliphatic ester of lactic acid corresponding to one lactide enantiomer and the aliphatic ester of lactyllactic acid corresponding to the other lactide enantiomer from the enzyme, and recycling the enzyme to the process; separating the aliphatic ester of lactic acid from the aliphatic ester of lactyllactic acid by fractional distillation; and either, where the aliphatic ester of lactyllactic acid is an aliphatic ester of S,S-lactyllactic acid, hydrolysing the aliphatic ester of S,S-lactyllactic acid to produce S-lactic acid or, where the aliphatic ester of lactic acid is an aliphatic ester of S-lactic acid, hydrolysing the aliphatic ester of S-lactic acid to produce S-lactic acid. Preferably, the mixture of R,R- and S,S-lactide used in the process has been prepared from a mixture of R- and S-lactic acid. The S-lactic acid produced by the process preferably has an enantiomeric excess of at least 90%, more preferably at least 95%, still more preferably at least 98%, most preferably at least 99%.

Alternatively, according to a second further embodiment of the present invention there is provided a process for producing R,R-lactide characterised by the steps of contacting a mixture of R,R- and S,S-lactide with an aliphatic alcohol (e.g. a $C_1$ to $C_8$ alkyl alcohol) and an enzyme to produce a mixture comprising aliphatic ester of lactic acid corresponding to one lactide enantiomer, and aliphatic ester of lactyllactic acid corresponding to the other lactide enantiomer; separating the mixture comprising aliphatic ester of lactic acid corresponding to one lactide enantiomer and the aliphatic ester of lactyllactic acid corresponding to the other lactide enantiomer from the enzyme, and recycling the enzyme to the process; separating the aliphatic ester of lactic acid from the aliphatic ester of lactyllactic acid by fractional distillation; and either, where the aliphatic ester of lactyllactic acid is an aliphatic ester of R,R-lactyllactic acid, converting the aliphatic ester of R,R-lactyllactic acid to R,R-lactide or, where the aliphatic ester of lactic acid is an aliphatic ester of R-lactic acid, converting the aliphatic ester of R-lactic acid to R,R-lactide. Preferably. the mixture of R,R- and S,S-lactide used in the process has been prepared from a mixture of R- and S-lactic acid. The R,R-lactide produced by the process preferably has an enantiomeric excess of at least 90%, more preferably at least 95%, still more preferably at least 98%, most preferably at least 99%.

Alternatively in a third further embodiment of the present invention there is provided a process for producing R-lactic acid characterised by the steps of: contacting a mixture of R,R- and S,S-lactide with an aliphatic alcohol (e.g. a $C_1$ to $C_8$ alkyl alcohol) and an enzyme to produce a mixture comprising aliphatic ester of lactic acid corresponding to one lactide enantiomer, and aliphatic ester of lactyllactic acid corresponding to the other lactide enantiomer; separating the mixture comprising aliphatic ester of lactic acid corresponding to one lactide enantiomer and the aliphatic ester of lactyllactic acid corresponding to the other lactide enantiomer from the enzyme, and recycling the enzyme to the process; separating the aliphatic ester of lactic acid from the aliphatic ester of lactyllactic acid by fractional distillation; and either, where the aliphatic ester of lactyllactic acid is an aliphatic ester of R,R-lactyllactic acid, hydrolysing the aliphatic ester of R,R-lactyllactic acid to produce R-lactic acid or, where the aliphatic ester of lactic acid is an aliphatic ester of R-lactic acid, hydrolysing the aliphatic ester of R-lactic acid to produce R-lactic acid. Preferably. the mixture of R,R- and S,S-lactide used in the process has been prepared from a mixture of R- and S-lactic acid. The R-lactic acid produced by the process preferably has an enantiomeric excess of at least 90%, more preferably at least 95%, still more preferably at least 98%, most preferably at least 99%.

Alternatively, in a fourth further embodiment there is provided a process for producing S,S-lactide characterised by the steps of contacting a mixture of R,R- and S,S-lactide with an aliphatic alcohol (e.g. a $C_1$ to $C_8$ alkyl alcohol) and an enzyme to produce a mixture comprising aliphatic ester of lactic acid corresponding to one lactide enantiomer, and aliphatic ester of lactyllactic acid corresponding to the other lactide enantiomer; separating the mixture comprising aliphatic ester of lactic acid corresponding to one lactide enantiomer and the aliphatic ester of lactyllactic acid corresponding to the other lactide enantiomer from the enzyme, and recycling the enzyme to the process; separating the aliphatic ester of lactic acid from the aliphatic ester of lactyllactic acid by fractional distillation; and either, where the aliphatic ester of lactyllactic acid is an aliphatic ester of S,S-lactyllactic acid, converting the aliphatic ester of S,S-lactyllactic acid to S,S-lactide or, where the aliphatic ester of lactic acid is an aliphatic ester of S-lactic acid, converting the aliphatic ester of S-lactic acid to S,S-lactide. Preferably. the mixture of R,R- and S,S-lactide used in the process has been prepared from a mixture of R- and S-lactic acid. The S,S-lactide produced by the process preferably has an enantiomeric excess of at least 90%, more preferably at least 95%, still more preferably at least 98%, most preferably at least 99%.

Conversion of the mixture of R- and S-lactic acid into a mixture of R,R and S,S-lactide may result in formation of R,S-lactide, as well as R,R- and S,S-lactide. If desired, R,S-lactide may be separated from R,R- and S,S-lactide by routine methods well known in the art.

Preferably the R,R- and S,S-lactides produced in respectively the second or fourth further embodiments set out above are separately polymerised to produce substantially optically pure PDLA or PLLA. PDLA and PLLA can be combined in varying proportions, for example using melt blending, to produce a range of stereocomplex polylactic acid formulations having an associated range of improved optical and form stability properties relative to either PLLA or PDLA alone. Whilst the relative proportions of these two polymers can vary widely it is preferred that the PLLA content of these formulations lie in the range 40 to 60% based on the total weight of PLLA and PDLA. The stereocomplex polymers so produced can be used in a wide range of applications, including a wider scope of durable uses previously not possible with PLLA.

The invention will now be illustrated by reference to the following examples.

EXAMPLES 1-3

Stereoselective Alcoholysis of Rac-Lactide in Heptane/THF (Batch)

A glass reactor was charged with racemic lactide (1 equivalent), n-butanol (1.5 equivalents), Novozym 435 (3% by weight of the racemic lactide) and varying amounts of a 90:10 (by weight) heptane/THF co-solvent (volumes based on the amount of n-butanol used). The mixture was stirred for 24 hours at room temperature and then analysed by chiral HPLC and NMR spectroscopy for R-n-butyl lactate, S-n-butyl lactate, S,S-n-butyl lactyllactate and R,R n-butyl lactyllactate, so that the composition of the lactate components could be determined. The results are shown in the following table (Nd=not detected):

| Example No. | Volume of heptanes/THF | % R-n-butyl lactate | % S-n-butyl lactate | % S,S-n-butyl lactyllactate | % R,R-n-butyl lactyllactate |
|---|---|---|---|---|---|
| 1 | 0 | 28 | Nd | 15 | 57 |
| 2 | 3.5 | 26 | Nd | 20 | 54 |
| 3 | 1.0 | 26 | Nd | 19 | 55 |

EXAMPLES 4-7

Stereoselective Alcoholysis of Rac-Lactide in Butanol (Batch)

In a series of experiments 2.89 g of racemic lactide, 100 mg of Novozym 435 (3.5% by weight lactide) and varying quantities of n-butanol (1.5 to 10 equivalents based on the racemic lactide) were mixed together in a glass reactor and stirred for a period of 60° C. for period of up to 24 hours. Samples were removed at varying times and analysed by chiral HPLC and NMR for the presence of R- and S-n-butyl lactate. Using this information % yields of R-n-butyl lactate based on the R,R-component of the racemic lactide starting material were calculated and reported in the following table. In all cases no S-n-butyl lactate was detected and no yields are therefore reported.

|  |  | Yield of R-n-butyl lactate | | | | | |
|---|---|---|---|---|---|---|---|
| Example | Time (h) | 1.5 eq | 2 eq | 2.5 eq | 3 eq | 6 eq | 10 eq |
| 4 | 2 | 43.5% | 67% | 57.5% | 45% | 38.5% | 39.5% |
| 5 | 5 | 57% | 77.5% | 81% | 82% | 46% | 44% |
| 6 | 7 | 55% | 76.5% | 90% | 96.5% (after 8 hours) | 92.5% | 86.5% |
| 7 | 24 | 59% | 77% | 89% | Not measured | 99.5% | 97% |

EXAMPLE 8

Distillation to Separate Butanol, Butyl Lactate and Butyl Lactyl Lactate 150 g racemic n-butyl lactyllactate was gently stirred at 50° C. in the presence of 7.5 g Novozym 435 (5% by weight of substrate) and 195 ml n-butanol for 6 hours, taking the conversion of (R,R)-n-butyl lactyllactate into (R)-n-butyl lactate to in excess of 95%. The immobilised enzyme was then removed by filtration and the bulk of the excess n-butanol removed by rotary evaporation at 50° C./25 mbar. A portion of the residue (100 ml) was transferred to a round-bottomed flask equipped with a distillation column packed with Raschig rings, a still-head and condenser. Distillation was then carried out at 30 mbar, the vacuum being maintained by a Vacuubrand CVC 2000 controller.

Fractions were collected as summarised in the Table below. Fractions 4 and 5 contained mixtures of (R)-n-butyl lactate and (S,S)-n-butyl lactyllactate, highlighting the difficulty in achieving separation of these components. Fractions 2 and 3 contained (R)-n-butyl lactate but no n-butyl lactyllactate. Fraction 3 contained (R)-n-butyl lactate in >98% ee. The results demonstrate that separation of alkyl lactate from alkyl lactylactate by distillation is possible without significant loss of enantiomeric purity.

| Fraction | Still-head temperature range (° C.) | Mass of fraction (g) | Composition of fraction |
|---|---|---|---|
| Post-reaction | — | 90.0 | n-butanol (excess - not measured) (R)-n-butyl lactate (49%) (R,R)-n-butyl lactyllactate (1%) (S,S)-n-butyl lactyllactate (50%) |
| 1 | 50-52 | 29.0 | n-butanol (99%) (R)-n-butyl lactate (1%) |
| 2 | 52-100 | 7.4 | n-butanol (38%) (R)-n-butyl lactate (62%) |
| 3 | 100 | 22.1 | (R)-n-butyl lactate (>99%) |
| 4 | 100-154 | 14.7 | (R)-n-butyl lactate (34%) (R,R)-n-butyl lactyllactate (3%) (S,S)-n-butyl lactyllactate (63%) |
| 5 | 154-160 | 11.6 | n-butanol (0.2%) (R)-n-butyl lactate (0.2%) |

-continued

| Fraction | Still-head temperature range (° C.) | Mass of fraction (g) | Composition of fraction |
|---|---|---|---|
| Pot residue | — | 4.7 | (R,R)-n-butyl lactyllactate (2%) (S,S)-n-butyl lactyllactate (97%) (S,S)-n-butyl lactyllactate (»90%) Higher oligomers («10%) |

EXAMPLE 9

Analogous experiments to those described in Examples 1 to 7 were carried out using IMMCALB-T2-150, IMMCALBY-T2-150, IMMCALB-T1-350, or a cross-linked aggregate of lipase B from *Candida antarctica*, as the enzyme in place of Novozym 435. Those enzymes showed similar levels of stereoselectivity to Novozym 435.

EXAMPLE 10

Stereoselective Alcoholysis of Rac-Lactide in Butanol/Acetone Mixture (Batch)

A glass vessel was charged with rac-lactide (2.30 g), Novozym 435 (115 mg, 5 wt % with respect to lactide), n-butanol (2.9 ml, 2:1 molar ratio with respect to lactide) and acetone (6.8 ml). The mixture was shaken by hand at RT to 45° C. to ensure that the lactide dissolves. Then the vessel was placed in a heated shaker 45° C., 750 rpm (t=0). The reaction was monitored over 24 hrs. Samples were analysed by chiral gas chromatography to determine the (S)-butyl lactate, (R)-butyl lactate, (S,S)-butyl lactyllactate, (R,R)-butyl lactyllactate, (S,S)-lactide and (R,R)-lactide composition. After 24 hrs the reaction reached 89% conversion to (S)-butyl lactate at an optical purity>99% e.e.

EXAMPLE 11

Stereoselective Alcoholysis of Rac-Lactide in Butanol/Acetone Mixture with Recycle of Enzyme (Batch)

Rac-lactide (1.45 g, 10 mmol) was alcoholised with n-BuOH (2.75 ml, 30 mmol, 3 eq.) and Novozym 435 (200 mg, 14%) for 7 h at 35° C. in the presence of 2.75 ml of acetone. After 7 h the reaction was stopped and analysed for conversion to R-butyl lactate. The reaction liquors were then carefully separated from the immobilised enzyme by syringe and the enzyme was washed with solvent and reused in a subsequent run. The enzyme was reused for 8 repeat runs. Conversion to R-butyl lactate after the $1^{st}$ run was 92% (of the theoretical yield) and conversion after the $8^{th}$ run was 79%.

EXAMPLE 12

Stereoselective Alcoholysis of Rac-Lactide in Butanol/Acetone Mixture with Recycle of Enzyme (Continuous)

At regular intervals a 50:50 mixture of (S,S)- and (R,R)-lactide was dissolved in acetone at a concentration of 30% wt lactide in a 1 litER water heated jacketed vessel at 45° C. equipped with a reflux condenser. n-Butanol was then added to the lactide solution so that the n-BuOH/lactide molar ratio was 2:1 at 45° C.; under these conditions the lactide remains in solution. Typical batches were prepared to supply the reaction rig with sufficient substrate to operate for at least 24 h.

The contents were then fed through a 400 mm length reflux column, the exterior collar of which was heated to 45° C. using recirculated heated water. The column was fitted directly onto a glass adaptor containing a 5 g packed bed of Novozym 435 (supported *Candida antarctica* Lipase B). The solution was fed through the column using a Watson Marlow 120S peristaltic pump and 1.6 mm ID Marprene tubing. Once passed through the enzyme bed the product mixture was collected and samples analysed by gas chromatography. Flow of reactants over the enzyme bed was adjusted to achieve a conversion of (R,R)-butyl lactyllactate into R-butyl lactate in the region 80-90%. Even after three months continuous operation conversions were >80% and the optical purity of the R-butyl lactate>99% e.e.

EXAMPLE 13

Stereoselective Alcoholysis of Rac-Lactide in Butanol/Methyl Ethyl Ketone (MEK) Mixture with Recycle of Enzyme (Continuous)

A solution of 10 g rac-lactide, 15 g BuOH, (3 Eq), and 50 g MEK (a ratio of 1:1.5:5) was passed through a steel column containing 0.500 g Novozym 435 immobilised *Candidia antarctica* Lipase B over a period of 60 h. Samples for analysis were taken at 2 hourly intervals from the feed and from the output of the column and the concentrations of (S)-butyl lactate, (R)-butyl lactate, (S,S)-butyl lactyllactate, (R,R)-butyl lactyllactate, (S,S)-lactide and (R,R)-lactide were determined by chiral liquid chromatography (no S-butyl lactate was detected). The conversion remained steady at 85% and the R-butyl lactate products were all >99% enantiomeric excess.

EXAMPLE 14

Distillation of Acetone and Butanol from Butyl Lactate and Butyl Lactyllactate

A 1 litER 3-necked glass flask was fitted with a magnetic stirrer bar and an insulated 20-plate Oldershaw column surmounted by a Perkin vacuum still head with 250 ml receiver. A feed point approximately half-way up the column allowed feedstock to be charged via a peristaltic pump using PharMed® BPT peristaltic tubing. The flask was heated using an oil bath and vacuum was applied via a Teflon diaphragm pump, with a solid $CO_2$ cooled trap.

The feedstock for this distillation consisted of acetone (49% wt); (R)-n-butyl lactate (21% wt); butanol (7% wt); (R,R)-n-butyl lactyllactate (3% wt) and (S,S)-n-butyl lactyllactate (19% wt). The remaining components included trace quantities of (S)-n-butyl lactate and both (S,S)- and (R,R)-lactides.

Initially, some extra butanol was added to the feed charged in order to establish continuous distillation conditions, since the amount of butanol present in the feedstock was low. Once this had been established (oil bath ~135° C., internal temp. ~117° C., still head temp. ~77° C., vacuum=500 mBarA), the main feed was then charged at 2.5-5.0 ml/min. Fractions were collected as detailed below and analysed by chiral GC.

| Fraction | Oil bath temp/ ° C. | Internal temp/ ° C. | Head temp. (° C.) | Vacuum (mBarA) | Mass of fraction (g) | Composition by GC (%) | | |
|---|---|---|---|---|---|---|---|---|
| | | | | | | Acetone | Butanol | (R)-Butyl lactate |
| a) | 135-149 | 117-135 | 70-76 | 500 | 45.3 | 99.5 | 0.0 | 0.5 |
| b) | 148-154 | 136-148 | 36-66 | 500 | 25.1 | 98.6 | 0.9 | 0.5 |
| c) | 147-153 | 138-147 | 30-36 | 500 | 10.1 | 96.1 | 3.4 | 0.5 |

From the 702 ml (609.5 g) of feedstock used, the composition of the resulting concentrated product (340.11 g) was: acetone (4.5%); (R)-n-butyl lactate (44.3%); n-butanol (4.7%); (R,R)-n-butyl lactyllactate (5.9%), (S,S)-n-butyl lactyllactate (39.0%) and (S)-n-butyl lactate (0.7%) with the remainder being (S,S)- and (R,R)-lactides.

The composition of the volatile products collected in the cold trap (59.7 g) was: acetone (89%) and butanol (10%) with the remaining 1% being n-butyl lactate.

A continuous distillation set up was constructed comprising a 250 ml Hastelloy reboiler (with sightglass), a trace-heated 20-plate Oldershaw column surmounted by a Perkin vacuum still head with 250 ml receiver. There was a feed point approximately half-way up the column allowing feedstock to be charged via a peristaltic pump using PharMed® BPT peristaltic tubing. The temperature of the reboiler and column heat tracing were electrically controlled. Vacuum was applied via a Teflon diaphragm pump, with a solid $CO_2$ cooled trap.

The feedstock for this distillation (1050.0 g) consisted of: acetone (49% wt); (R)-n-butyl lactate (21% wt); butanol (7% wt); (R,R)-n-butyl lactyllactate (3% wt) and (S,S)-n-butyl lactyllactate (19% wt) with traces of (S)-n-butyl lactate and both (S,S)- and (R,R)-lactides.

After the initial filling and conditioning of the column, the feedstock was fed in and rates and temperatures adjusted until steady continuous distillation was achieved. The optimum conditions were found to be vacuum=100 mBarA; Reboiler temperature=100° C.; Heat tracing=65° C.; Feed rate=4 ml/min.

These conditions were maintained throughout this distillation, and resulted in the product distribution detailed below. This procedure successfully concentrated the higher-boiling components (mainly (R)-n-butyl lactate and (S,S)-n-butyl lactyllactate) in the reboiler in high yields. Acetone and butanol recovery is also high and these solvents may be recycled to earlier stages of the overall process.

| Details | Amount (g) | Composition by GC (%) | | | | | | |
|---|---|---|---|---|---|---|---|---|
| | | Acetone | Butanol | (S)-BuLa | (R)-BuLa | (S,S)-BuLaLa | (R,R)-BuLaLa | (S,S)-Lactide | (R,R)-Lactide |
| Feed-Stock | 1050.0 | 48.1 | 7.8 | 0.1 | 21.6 | 19.4 | 2.7 | 0.1 | 0.2 |
| Distillates | 63.4 | 11.0 | 53.6 | 0.2 | 28.9 | 5.6 | 0.8 | 0.0 | 0.0 |
| Reboiler Fractions | 335.3 | 0.4 | 3.5 | 0.2 | 45.0 | 44.3 | 6.3 | 0.1 | 0.3 |
| Cold Trap | 422.2 | 95.3 | 4.3 | 0.2 | 0.2 | 0.1 | 0.0 | 0.0 | 0.0 |
| Sampling | 126.8 | 4.6 | 10.3 | 0.7 | 24.9 | 24.4 | 3.5 | 0.0 | 0.2 |

BuLa = butyl lactate; BuLaLa = butyl lactyl lactate

EXAMPLE 15

Distillation of Butyl Lactate from Butyl Lactyllactate

A continuous distillation apparatus was constructed comprising a 250 ml Hastelloy reboiler with sightglass fitted with a heated 20-plate Oldershaw column surmounted by a Perkin vacuum still head with 250 ml receiver. There was a feed point approximately half-way up the column allowing feedstock to be charged via a peristaltic pump using PharMed® BPT peristaltic tubing. The temperature of the reboiler and column heat tracing were electrically controlled. Vacuum was applied via a Teflon diaphragm pump, with a solid $CO_2$ cooled trap.

The feedstock for this distillation (740.5 g) consisted of: acetone (<0.5%); (R)-n-butyl lactate (46%); butanol (3%); (R,R)-n-butyl lactyllactate (6%) and (S,S)-n-butyl lactyllactate (44%) with trace quantities (<0.5%) of (S)-n-butyl lactate and both (S,S)- and (R,R)-lactides.

After the initial filling and conditioning of the column, the feedstock was fed in and rates and temperatures adjusted until steady continuous distillation was achieved. The optimum conditions were found to be: Vacuum=35 mBarA; reboiler temperature=150° C.; Heat tracing=110° C.; Feed rate=1-4 ml/min. These conditions were maintained throughout this distillation, and resulted in the product distribution detailed below:

| Details | Mass (g) | Composition by GC (%) | | | | | | |
|---|---|---|---|---|---|---|---|---|
| | | Acetone | BuOH | (S)-BuLa | (R)-BuLa | (S,S)-BuLaLa | (R,R)-BuLaLa | (S,S)-Lactide | (R,R)-Lactide |
| Feed | 740.5 | 0.2 | 3.2 | 0.2 | 45.9 | 44.0 | 6.3 | 0.1 | 0.2 |
| Distillate | 277.6 | 0.0 | 5.0 | 0.4 | 93.9 | 0.5 | 0.1 | 0.0 | 0.1 |
| Reboiler Fractions | 389.6 | 0.0 | 0.3 | 0.2 | 17.7 | 70.7 | 10.3 | 0.3 | 0.5 |
| Cold Trap | 10.6 | 12.0 | 76.1 | 0.9 | 10.8 | 0.1 | 0.0 | 0.0 | 0.0 |
| Sampling | 53.1 | 2.6 | 0.7 | 0.2 | 16.1 | 69.5 | 10.3 | 0.2 | 0.4 |

BuLa = butyl lactate; BuLaLa = butyl lactyl lactate

The distilled product analysed as 93.9% (R)-butyl lactate; 0.4% (S)-butyl lactate, 5.0% butanol; 0.5% (S,S)-butyl lactyllactate; 0.1% (R,R)-butyl lactyllactate and 0.1% (R,R)-lactide.

The invention claimed is:

1. A process for producing an aliphatic ester of lactic acid and an aliphatic ester of lactyllactic acid, one of said esters being in the R form and the other being in the S form, characterised by the steps of:
    (a) contacting a mixture of R,R- and S,S-lactide with an aliphatic alcohol and an enzyme to produce a mixture comprising the aliphatic ester of lactic acid corresponding to one lactide enantiomer (R or S) and the aliphatic ester of lactyllactic acid corresponding to the other lactide enantiomer (S or R);
    (b) separating the mixture comprising the aliphatic ester of lactic acid and the aliphatic ester of lactyllactic acid from the enzyme, and recycling the enzyme to the process; and
    (c) separating the aliphatic ester of lactic acid from the aliphatic ester of lactyllactic acid by fractional distillation.

2. The process as claimed in claim 1, wherein a solvent which is miscible with the aliphatic alcohol is employed in step (a).

3. The process as claimed in claim 1, wherein the aliphatic ester of lactic acid is separated from the aliphatic ester of lactyllactic acid by fractional distillation at a pressure of from 1,000 Pa to 5,000 Pa and at a temperature of from 50° C. to 120° C.

4. The process as claimed in claim 1, wherein the aliphatic ester of lactic acid separated by fractional distillation has an enantiomeric excess of at least 90%.

5. The process as claimed in claim 1, wherein the aliphatic ester of lactyllactic acid separated by fractional distillation has an enantiomeric excess of at least 90%.

6. The process as claimed in claim 1, wherein a $C_2$ to $C_8$ aliphatic alcohol is used in step (a).

7. The process as claimed in claim 6, wherein that the molar ratio of $C_2$ to $C_8$ aliphatic alcohol to racemic lactide is in the range 2:1 to 5:1.

8. The process as claimed in claim 6, wherein the $C_2$ to $C_8$ aliphatic alcohol is n-butanol.

9. The process as claimed in claim 1, wherein the enzyme is a *Candida antarctica* lipase B, and the aliphatic ester of lactic acid and the aliphatic ester of lactyllactic acid are respectively an aliphatic ester of R-lactic acid and an aliphatic ester of S,S-lactyllactic acid.

10. The process as claimed in claim 1, wherein the enzyme is chemically or physically immobilised on a porous support.

11. The process as claimed in claim 1, which comprises the further step of converting one or both of the aliphatic ester of lactyllactic acid and the aliphatic ester of lactic acid into the corresponding R,R- or S,S-enantiomer of lactide and/or the corresponding R- or S-enantiomer of lactic acid.

12. The process as claimed in claim 1, wherein the mixture of R,R- and S,S-lactide used in step (a) has been prepared from a mixture of R- and S-lactic acid.

13. The process as claimed in claim 12, wherein the mixture of R- and S-lactic acid has been prepared by treating a monosaccharide or glycerol with a base.

14. The process as claimed in claim 1 wherein the aliphatic ester of lactyllactic acid is an aliphatic ester of S,S-lactyllactic acid, the process comprises hydrolysing the aliphatic ester of S,S-lactyllactic acid to produce S-lactic acid or, where the aliphatic ester of lactic acid is an aliphatic ester of S-lactic acid, the process comprises hydrolysing the aliphatic ester of S-lactic acid to produce S-lactic acid.

15. The process as claimed in claim 1 wherein the aliphatic ester of lactyllactic acid is an aliphatic ester of R,R-lactyllactic acid, the process comprises hydrolysing the aliphatic ester of R,R-lactyllactic acid to produce R-lactic acid or, where the aliphatic ester of lactic acid is an aliphatic ester of R-lactic acid, the process comprises hydrolysing the aliphatic ester of R-lactic acid to produce R-lactic acid.

16. The process as claimed in claim 1 wherein the aliphatic ester of lactyllactic acid is an aliphatic ester of R,R-lactyllactic acid, the process comprises converting the aliphatic ester of R,R-lactyllactic acid to R,R-lactide or, where the aliphatic ester of lactic acid is an aliphatic ester of R-lactic acid, the process comprises converting the aliphatic ester of R-lactic acid to R,R-lactide.

17. The process as claimed in claim 16, wherein the R,R-lactide produced is polymerised to produce poly-R-lactic acid.

18. The process as claimed in claim 17, wherein the poly-R-lactic acid produced is melt blended to form stereocomplex polylactic acid.

19. The process as claimed in claim 1 wherein the aliphatic ester of lactyllactic acid is an aliphatic ester of S,S-lactyllactic acid, the process comprises converting the aliphatic ester of S,S-lactyllactic acid to S,S-lactide or, where the aliphatic ester of lactic acid is an aliphatic ester of S-lactic acid, the process comprises converting the aliphatic ester of S-lactic acid to S,S-lactide.

20. The process as claimed in claim 19, wherein the S,S-lactide produced is polymerized to produce poly-S-lactic acid.

21. The process as claimed in claim 20, wherein the poly-S-lactic acid producted is melt blended to form stereocomplex polylactic acid.

* * * * *